(12) United States Patent
Kim et al.

(10) Patent No.: US 11,062,790 B2
(45) Date of Patent: Jul. 13, 2021

(54) METHOD FOR THOROUGHLY DESIGNING VALID AND RANKED PRIMERS FOR GENOME-SCALE DNA SEQUENCE DATABASE

(71) Applicant: Daegu Gyeongbuk Institute of Science and Technology, Daegu (KR)

(72) Inventors: Min Soo Kim, Daegu (KR); Jae Hyung Koo, Daegu (KR); Hye Rin Kim, Seoul (KR); Na Na Kang, Daegu (KR); Kang Wook Chon, Gunsan-si (KR); Seon Ho Kim, Daejeon (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 981 days.

(21) Appl. No.: 14/824,678

(22) Filed: Aug. 12, 2015

(65) Prior Publication Data
US 2016/0306915 A1    Oct. 20, 2016

(30) Foreign Application Priority Data
Apr. 15, 2015 (KR) .......................... 10-2015-0052999

(51) Int. Cl.
*G01N 33/49* (2006.01)
*G16B 25/00* (2019.01)

(52) U.S. Cl.
CPC .................................... *G16B 25/00* (2019.02)

(58) Field of Classification Search
None
See application file for complete search history.

(56) References Cited

U.S. PATENT DOCUMENTS

2007/0269820 A1* 11/2007 Fielder ................ C12Q 1/6813
435/6.13

OTHER PUBLICATIONS

Huber, G. "Differences in the cellular distribution of two microtubule-associated proteins, MAP1 and MAP2, in the rat brain." J Neurosci 4 (1984): 151-160.*
Hyerin Kim, et al., "MRPrimer: a MapReduce-based method for the thorough design of valid and ranked primers for PCR Nucleic Acids Research" dated Jun. 24, 2015, pp. 1-10.

* cited by examiner

*Primary Examiner* — Anna Skibinsky
(74) *Attorney, Agent, or Firm* — Hauptman Ham, LLP

(57) ABSTRACT

A method for designing all coverage of valid primer pairs, which satisfy various filtering constraints provided by users with respect to a given sequence database and has validated specificity to given sequences, is provided. By screening all suitable primer pairs present on a given DNA sequence database without omitting any one primer pair and also screening all primers having a coverage of 1 or more as well as primers having a coverage of 1, a user can be allowed to give rankings to the primers in order to easily select the primers having a high success rate in biological experiments from the resulting primers.

6 Claims, 13 Drawing Sheets

Specification includes a Sequence Listing.

FIG. 9A

Map1 { ATGCCTAGACGG ... AATGATGACATTGCCAGCCA ···
              (A)
       ATGCCCCCTTCGGA ... AATCATAGTGTCTACAACTC ···
              (B)
       ⋮

⋈
Map2 { ATGGGAACACGGATC ... AATAATGACATTGCCAGACA ···
              (C)
       ATGCCTCAACCCTTCGGA ... AATGATAGTGTCAACAACTC ···
              (D)
       ⋮

FIG. 9B (i) #mismatch=1(seed size=9)        (ii) #mismatch=2(seed size=6)

(A) AATGATGACATTGCCAGCCA        (A) AATGATGACATTGCCAGCCA
(C) AATAATGACATTGCCAGACA        (C) AATAATGACATTGCCAGACA
(D) AATGATAGTGTCAACAACTC        (D) AATGATAGTGTCAACAACTC

⇩                              ⇩
NO COMMON SEED,            NO COMMON SEED, CHECKED,
SO, BUT (C) AND (D) PASS   (C) IS FILTERED OUT, AND (D) PASSES

SEQUENCE LISTING

```
<160> NUMBER OF SEQ ID NOS: 12

<210> SEQ ID NO 1
<211> LENGTH: 12
<212> TYPE: DNA
<213> ORGANISM: Artificial Sequence
<220> FEATURE:
<223> OTHER INFORMATION: Synthetic example sequence

<400> SEQUENCE: 1
atgcctagac gg                                                              12

<210> SEQ ID NO 2
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 2
aatgatgaca ttgccaagag                                                      20

<210> SEQ ID NO 3
<211> LENGTH: 15
<212> TYPE: DNA
<213> ORGANISM: Artificial Sequence
<220> FEATURE:
<223> OTHER INFORMATION: Synthetic example sequence

<400> SEQUENCE: 3
atgggaacac ggatc                                                           15

<210> SEQ ID NO 4
<211> LENGTH: 14
<212> TYPE: DNA
<213> ORGANISM: Artificial Sequence
<220> FEATURE:
<223> OTHER INFORMATION: Synthetic example sequence

<400> SEQUENCE: 4
atgccccctt cgga                                                            14

<210> SEQ ID NO 5
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 5
aatgatgaga ttgccaactg                                                      20

<210> SEQ ID NO 6
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 6
aatgaatgac atgtgcagac                                                      20

<210> SEQ ID NO 7
<211> LENGTH: 20
<212> TYPE: DNA
<213> ORGANISM: Artificial Sequence
```

```
<220> FEATURE:
<223> OTHER INFORMATION: Synthetic example sequence

<400> SEQUENCE: 7
aatgatgaca ttgccagcca                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 8
aatcatagtg tctacaactc                                              20

<210> SEQ ID NO 9
<211> LENGTH: 15
<212> TYPE: DNA
<213> ORGANISM: Artificial Sequence
<220> FEATURE:
<223> OTHER INFORMATION: Synthetic example sequence

<400> SEQUENCE: 9
atgggaacac ggatc                                                   15

<210> SEQ ID NO 10
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 10
aataatgaca ttgccagaca                                              20

<210> SEQ ID NO 11
<211> LENGTH: 18
<212> TYPE: DNA
<213> ORGANISM: Artificial Sequence
<220> FEATURE:
<223> OTHER INFORMATION: Synthetic example sequence

<400> SEQUENCE: 11
atgcctcaac ccttcgga                                                18

<210> SEQ ID NO 12
<211> LENGTH: 20
<212> TYPE: DNA
<213> ORGANISM: Artificial Sequence
<220> FEATURE:
<223> OTHER INFORMATION: Synthetic example sequence

<400> SEQUENCE: 12
aatgatagtg tcaacaactc                                              20
```

METHOD FOR THOROUGHLY DESIGNING VALID AND RANKED PRIMERS FOR GENOME-SCALE DNA SEQUENCE DATABASE

This application claims priority to and the benefit of Korean Patent Application No. 10-2015-0052999, filed on Apr. 15, 2015, the disclosure of which is incorporated herein by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 35068_00001_US_Sequence_Listing. The size of the text file is 3 KB, and the text file was created on Sep. 16, 2015.

BACKGROUND

Field of the Invention

The present invention relates to a method for designing primers, and more particularly, to a method for designing all coverage of valid primer pairs, which satisfies various filtering constraints provided by users with respect to a given sequence database and has validated specificity to given sequences.

Discussion of Related Art

Generally, a short single-stranded DNA serving as a starting point upon DNA synthesis is referred to as a primer. Such primers have been widely used for standard techniques in hospitals, research institutes, universities, and the like, which conduct DNA polymerase-related biological experiments such as DNA sequencing or polymerase chain reactions (PCRs).

FIG. 1 is a diagram showing a case in which a forward primer 205 and a reverse primer 203 bind respectively to a target forward template 201 and a target reverse template 207 serving as separated DNA strands 202 so that DNA polymerases can synthesize new DNA double strands.

As shown in FIG. 1, the new DNA synthesis of a reverse strand 204 and a forward strand 206 from both ends of the separated DNA strands 202 is performed in a 5' to 3' direction. As a method of rapidly amplifying a target DNA sequence with a proper set of primers, PCR may be used in various fields, which may, for example, include phylogenetic analysis of related genes between different species which are unknown or distantly related to each other, DNA gene tests for detecting the presence of genetic diseases and mutations, research on diagnosing diseases with infectious risk caused by HIV or antibiotic-resistant bacteria, forensic analysis using genetic fingerprints and paternity tests, research on population biology through the finding of microsatellites using molecular markers, etc.

Also, quantitative PCR (qPCR), also known as real-time PCR, has been widely used to determine the results of high-throughput experiments confirming the validity of changes in expression of selected genes. Here, the success in PCR-based experiments depends highly on the design of primers suitable for a target sequence.

Such prior arts have the following four limitations. First, they have a problem in that it is impossible to test primer design constraints and verify specificity. When primers are designed for a single sequence or multiples sequences, various constraints on the primers should be considered. For example, the single primer filtering constraints include the length of primers, temperature (° C.), GC content (%), self-complementarity, consecutive bases, and end stability ($\Delta G$ value), and the pair primer filtering constraints include the difference in length of a primer pair, the difference in temperature in a primer pair, product (amplicon) size, pair-complementarity, and 3' end pair-complementarity.

When the primers are manually designed in consideration of the above-described single primer filtering constraints and pair primer filtering constraints, a large amount of time is required, and inaccurate results may often be obtained. Therefore, many automated methods capable of testing the above-described single primer filtering constraints and pair primer filtering constraints to design proper primers have been devised.

However, the prior arts have a problem in that it is impossible to simultaneously verify the specificity to be further checked in addition to the primer design constraint. To verify the specificity, a homology test is performed on non-target sequences so that designed primers can amplify only a target sequence.

In conventional methods, this verification of the specificity is further performed for primers satisfying the constraints to partially solve the problem using a tool such as BLAST. Thus, users generally use two different developed tools together to test the primer design constraints and verify the specificity.

However, primer results satisfying both the various design constraints existing in a given sequence database and the verification of the specificity have not been obtained. Second, since conventional methods for designing one target sequence are used to design primers for only a certain target sequence, they have problems in performing a qPCR experiment requiring several tens to several hundreds of primers which satisfy the same conditions.

qPCR is an experimental method that is widely used to analyze an expression level of a gene, and thus primers that satisfy the same strict constraints (for example, the size of the very similar product size) on a genomic scale and have verified specificity are required.

Up to now, the amplification of a non-target sequence is a problem often occurring in qPCR experiments. Since this problem becomes more serious when primers do not satisfy the same constraints, conventional techniques focus on designing the primers satisfying the same conditions for a small amount of sequence data. However, the primers designed by such conventional techniques are not suitable in qPCR experiments effective for analyzing a gene expression level on a large scale since the specificity of the primers is not verified through a complicated comparison process.

Third, when primers are designed for multiple sequences, the conventional techniques have a problem in that it is difficult to screen all valid primers even when the valid primers exist in the sequence database. This is because the first step of multiple sequence alignment (MSA) is a heuristic method. Since complexity of optimal MSA is essentially NP-complete, it is impossible to perform an optimal MSA for several very small sequences in an aspect of use of a computer. Therefore, a heuristic method is used in most MSA tools such as CLUSTALW, and thus the primers designed based on the MSA results are not complete.

In addition, although the optimal MSA may be obtained for any given sequence, it is difficult to completely screen all possible primers in one fixed alignment. This is because some primers are found in a conserved region in the non-optimal MSA. Since all the valid primers are not screened using the conventional techniques based on such a heuristic method, the conventional techniques have a problem in that the primers required in experiments, such as qPCR, which requires a number of valid primers, are not provided when particular primers inherent in families and sequences having a high homology such as olfactory receptors are rare.

Fourth, in the case of conventional methods for screening a number of target sequences, degenerate primers that are a set of similar primers for genes for which it is difficult to design primers are designed to solve such a problem. However, they have a problem in that the accuracy of PCR amplification is low. The degenerate primers should essentially have the balance between degeneracy and coverage.

Generally, when the degeneracy of primers is set to be very high, the accuracy of PCR amplification may become low. Also, current research results show that the degenerate primers are not very effective. Since the use of degenerate primers results in some level of biased results in phylogenetic research, a profile used may not exactly define a range of species groups. The use of non-degenerate primers makes it possible to obtain the same high-quality taxonomic category as the use of the degenerate primers.

SUMMARY OF THE INVENTION

The present invention is designed to solve the problems of the prior art, and therefore it is an object of the present invention to provide a method for designing all coverage of valid primers, which satisfies various filtering constraints provided by users with respect to a given sequence database and satisfies the conditions for specificity to large-scale DNA sequences in a large-scale DNA sequence database used to design all coverage of valid primer pairs having validated specificity to given DNA sequences.

To realize a specific solution to the problems in the prior art presented above, first, a solution to the first problem in the prior art is to design valid primer pairs that satisfy all given constraints and conditions for specificity with respect to respective target sequences through large-scale complicated joining between candidate primer sets designed from each of target sequences and all subsequences extractable from all input sequences, that is, that pass validations.

A solution of the present invention to the second problem in the prior art is to find all coverage of valid primer pairs which satisfies the same constraints on several tens to hundreds of thousands of input sequences and thereby directly use the valid primer pairs in experiments such as qPCR.

Also, a solution of the present invention to the third problem in the prior art is to find all valid primers without omitting any one valid primer using a key value-based join method in which a MapReduce framework is provided without depending on sequence alignments or any heuristic rule-based methods (the number of primer results is in the tens of millions).

Finally, a solution of the present invention to the fourth problem in the prior art is to find primers having a coverage of 1 or more as well as primers having a coverage of 1, that is, all non-degenerate primers, which can amplify a number of target sequences, without omitting any one non-degenerate primer, thereby presenting users with the primer results which satisfy both coverage and accuracy in PCR experiments.

According to an aspect of the present invention, there is provided a method for designing all coverage of valid primers which satisfies the conditions for specificity to large-scale DNA sequences in a large-scale DNA sequence database. The method may include receiving a given DNA sequence database to extract partial sequences for candidate primers having all possible lengths between the minimum length and the maximum length (operation 1); excluding the primers which do not satisfy input single filtering conditions when the candidate primers extracted in operation 1 are subjected to the single filtering conditions (operation 2); pair-joining Map1, which includes all the possible partial sequences obtained in operation 1, and Map2, which includes candidate primer sets satisfying the single filtering conditions obtained in operation 2, and removing the primers for Map2 when the primers for Map1 and Map2 have the same sequences other than the 5' termini thereof (operation 3); pair-joining Map1, which includes all the possible partial sequences obtained in operation 1, and Map2, which includes candidate primer sets satisfying the single filtering conditions and 5' cross-hybridization filtering conditions obtained in operation 3, and removing the primers for Map2 when the primers for Map1 have the same sequences as the primers for Map2 except the sequences having a given mismatch number (#mismatch) (operation 4); removing false-positive primers which still remain from the results of operation 4 and do not satisfy general cross-hybridization filtering conditions (operation 5); dividing the primers remaining from the results of operation 5 into forward primer sets and reverse primer sets and excluding the primers which do not satisfy the filtering conditions for self-join calculation when the divided forward and reverse primer sets are subjected to the filtering conditions (operation 6); and calculating penalty scores for the primer pairs passing operation 6, and sorting the primer pairs in the same sidset groups according to the calculated penalty scores (operation 7).

Operation 1 may include receiving the DNA sequence database in a format of a <k1:sid, v1:S> pair of a sequence identification number sid and sequence data S and extracting the subsequences for candidate primers having all possible lengths between the minimum length and the maximum length; tagging and extracting reverse complementary primers with respect to the extracted primers; and generating sidsets as sets of sids represented by the same primers and converting a format of the sidsets.

Operation 2 may include excluding the primers which do not satisfy the plurality of single filtering conditions when the primers are subjected to the plurality of single filtering conditions.

The plurality of single filtering conditions may include temperature (° C.), GC content (%), self-complementarity, 3'-end self-complementary consecutive bases, and end stability (a $\Delta G$ value).

Operation 3 may include receiving both of the Map1, which includes all the possible partial sequences extracted from the given DNA sequence database, and the Map2, which includes candidate primer sets satisfying the single filtering conditions, and dividedly storing subsequences having a certain length at the 5' termini thereof provided by a user, and the rest subsequences; and removing the primers for Map2, when the primers for Map1 have the same sequences as the primers for Map2 except the 5' terminal region thereof, while pair-joining the Map1 and the Map2.

Operation 4 may include receiving both of the Map1, which includes all the possible partial sequences extracted from the given DNA sequence database, and the Map2, which includes candidate primer sets satisfying the single filtering conditions and the 5' cross-hybridization filtering conditions, dividing each of the Map1 and the Map2 into a plurality of seeds, and storing the plurality of seeds; and removing the primers for Map2 when the primers for Map1 have the same sequences as the primers for Map2 except the sequences having a given mismatch number (#mismatch), while pair-joining the Map1 and the Map2.

Operation 5 may include removing the corresponding primers when one of lists (v2:filtered) collected as the same k2:sidset⊕P⊕sid⊕pos is proven to be false.

Operation 6 may include grouping the candidate primers having the same sids through format conversion; dividing the candidate primers belonging to the group into two sets of unlabeled forward primers and labeled reverse primers according to a label introduced when the candidate primers are extracted from the DNA sequence database; and removing the primers which do not satisfy a plurality of pair primer filtering conditions when the primers are subjected to the plurality of pair primer filtering conditions.

The plurality of pair primer filtering conditions may include the difference in length, the difference in temperature, a product length, pair-complementarity and 3' pair-complementarity.

Operation 7 may include calculating penalty scores of the forward and reverse primers which correspond to single primer filtering conditions; calculating a pair primer penalty score corresponding to the pair primer filtering conditions and adding the pair primer penalty score to the sum of the two calculated penalty scores; grouping the primers according to the same sidsets and sending the primers to a certain Reduce; giving the order for the grouped primers based on the added penalty scores; and converting an output format of the grouped primers whose orders are given.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIGS. 9A and 9B are schematic diagrams showing an application of the operations (S306 and S308) as shown in FIG. 3;

in FIG. 9A: Map 1, upper row ATGCCTAGACGG is SEQ ID NO: 1 and AATGATGACATTGCCAGCCA is SEQ ID NO: 7, lower row—ATGCCCCCTTCGGA is SEQ ID NO: 4 and AATCATAGTGTCTACAACTC is SEQ ID NO: 8;

Figure 3:
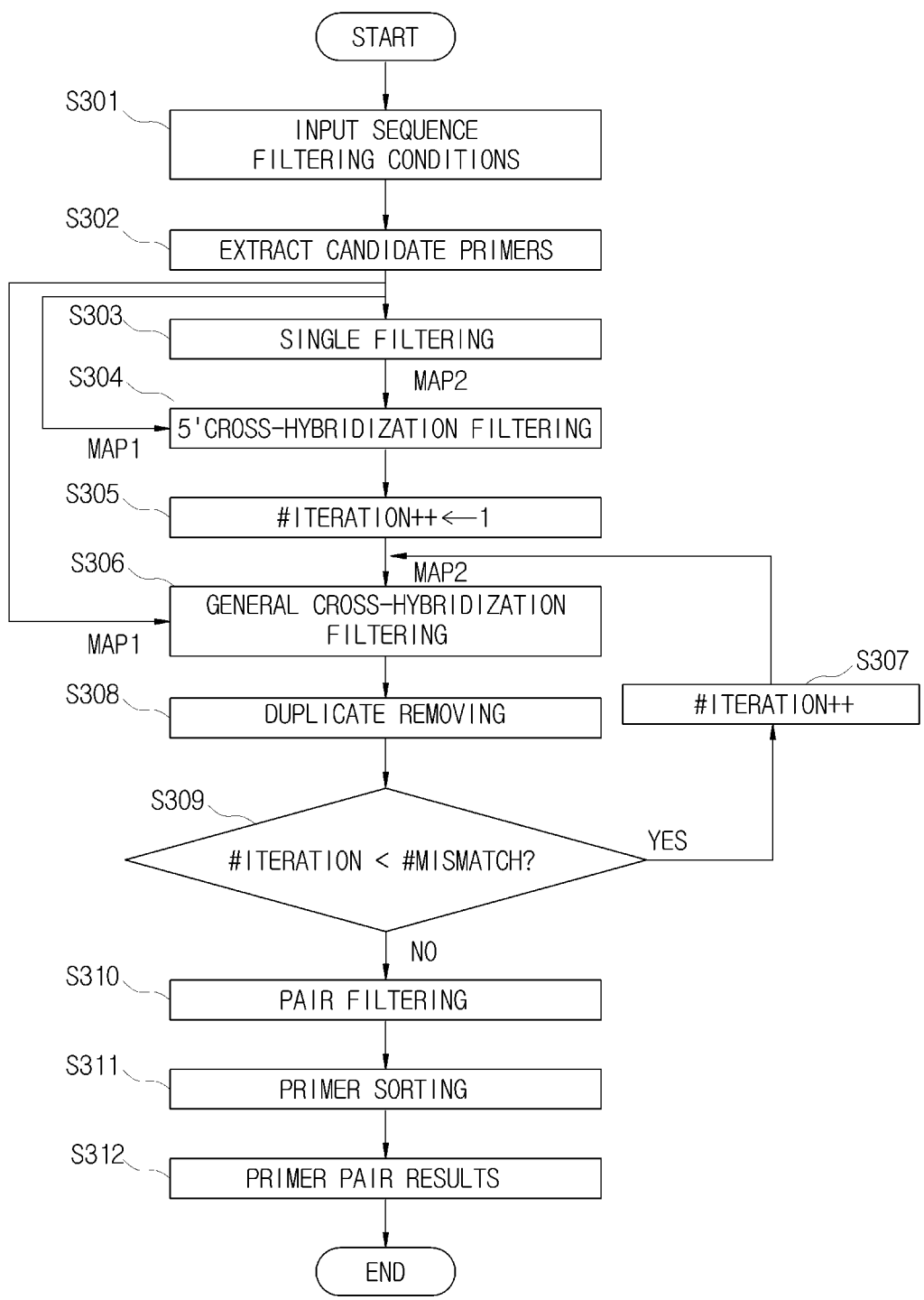
FIG. 3 is a flowchart showing a method of designing all valid primers which satisfy the conditions for specificity to large-scale DNA sequences in a large-scale DNA sequence database according to one exemplary embodiment of the present invention.
Figure 10:
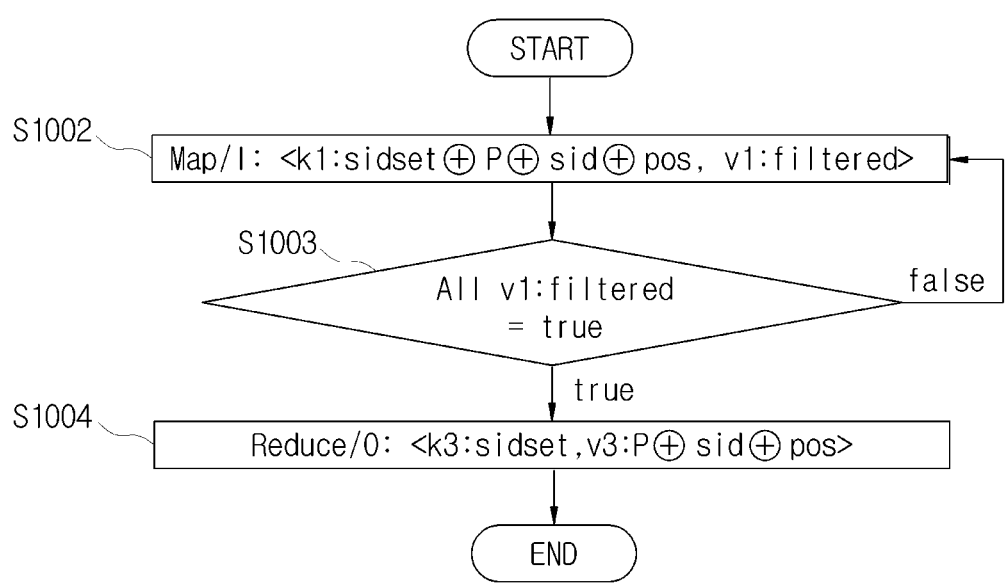
Figure 11:
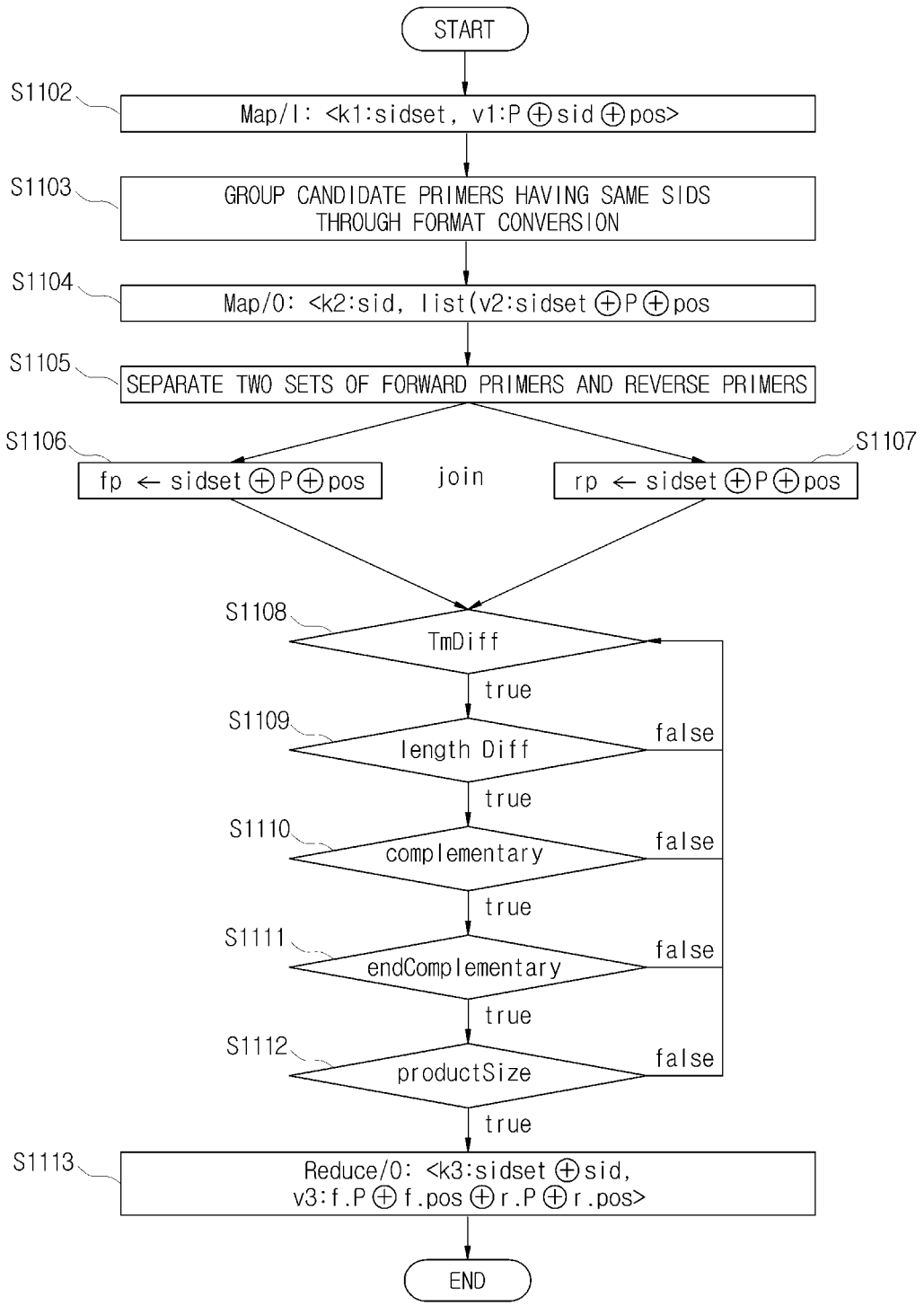
Figure 12:
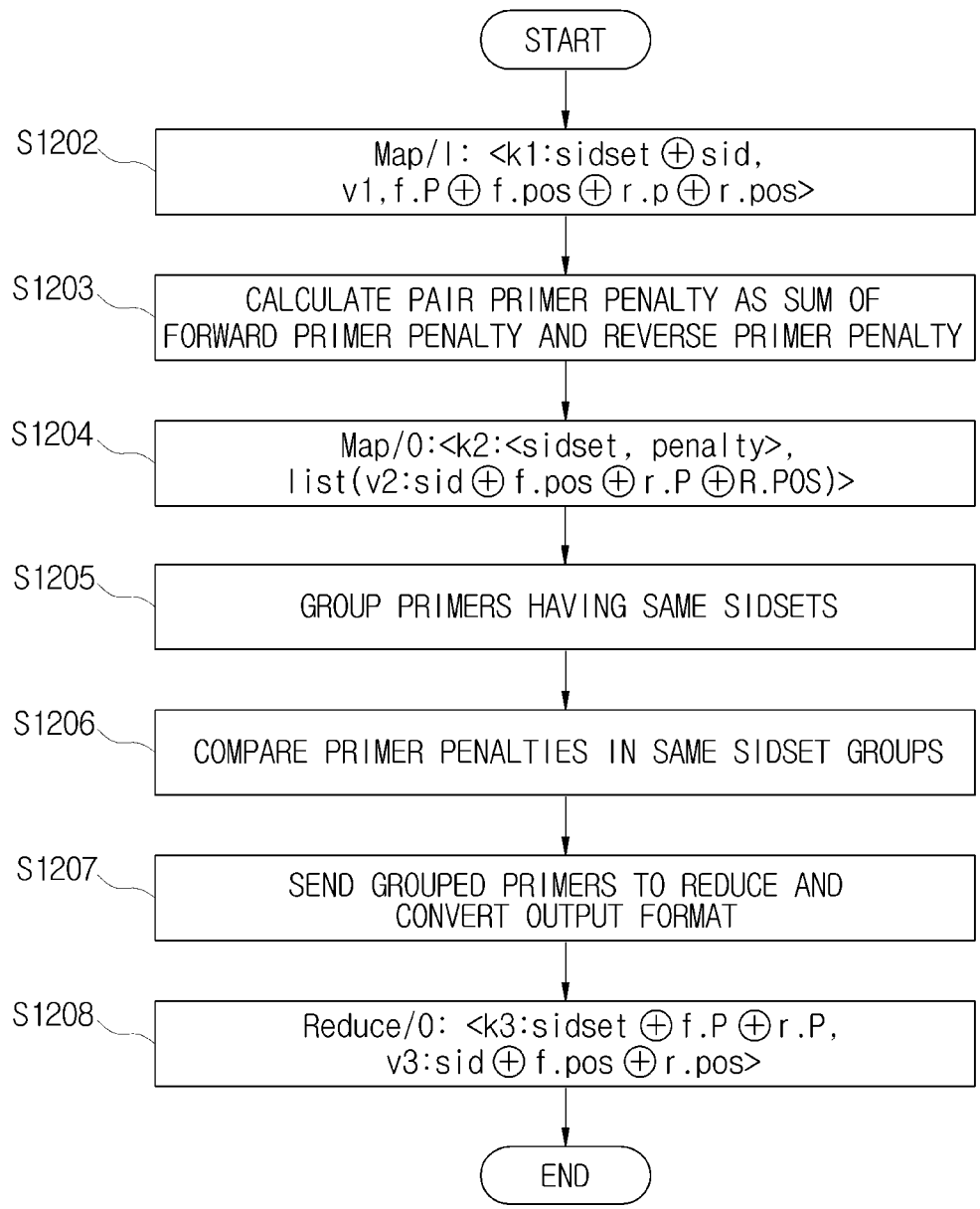

Map 2, upper row—ATGGGAACACGGATC is SEQ ID NO: 9 and AATAATGACATTGCCAGACA is SEQ ID NO: 10; lower row—ATGCCTCAACCCTTCGGA is SEQ ID NO: 11 and AATGATAGTGTCAACAACTC is SEQ ID NO: 12; and in FIG. 9B: left column—AATGATGACATTGCCAGCCA is SEQ ID NO: 7, AATAATGACATTGCCAGACA is SEQ ID NO: 10 and AATGATAGTGTCAACAACTC is SEQ ID NO: 12, and right column—AATGATGACATTGCCAGCCA is SEQ ID NO: 7, AATAATGACATTGCCAGACA is SEQ ID NO: 10 and AATGATAGTGTCAACAACTC is SEQ ID NO: 12;

FIG. 10 is a detailed flowchart of a duplicate removing operation (S308) as shown in FIG. 3;

FIG. 11 is a detailed flowchart of a pair filtering operation (S310) as shown in FIG. 3; and FIG. 12 is a detailed flowchart of a primer sorting operation (S311) as shown in FIG. 3.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

Hereinafter, the method for designing all coverage of valid primers which satisfies the conditions for specificity to large-scale DNA sequences in a large-scale DNA sequence database will be described in detail.

Figure 1:
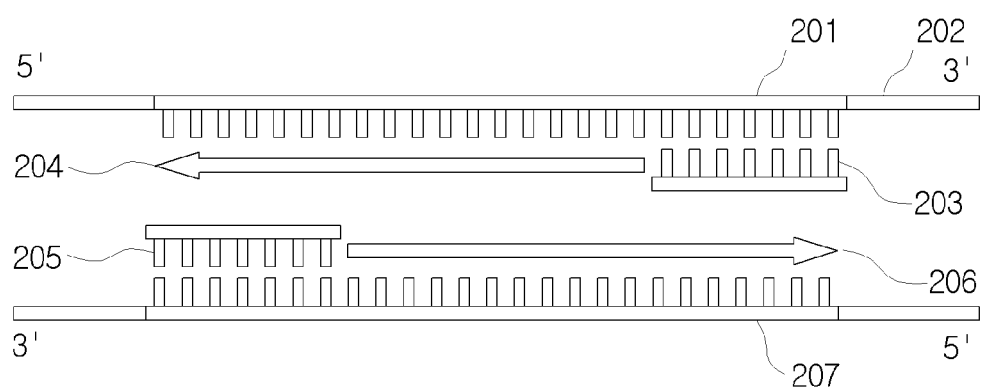
FIG. 1 is a diagram showing a target sequence to which general forward and reverse primers are bound.
Figure 2:
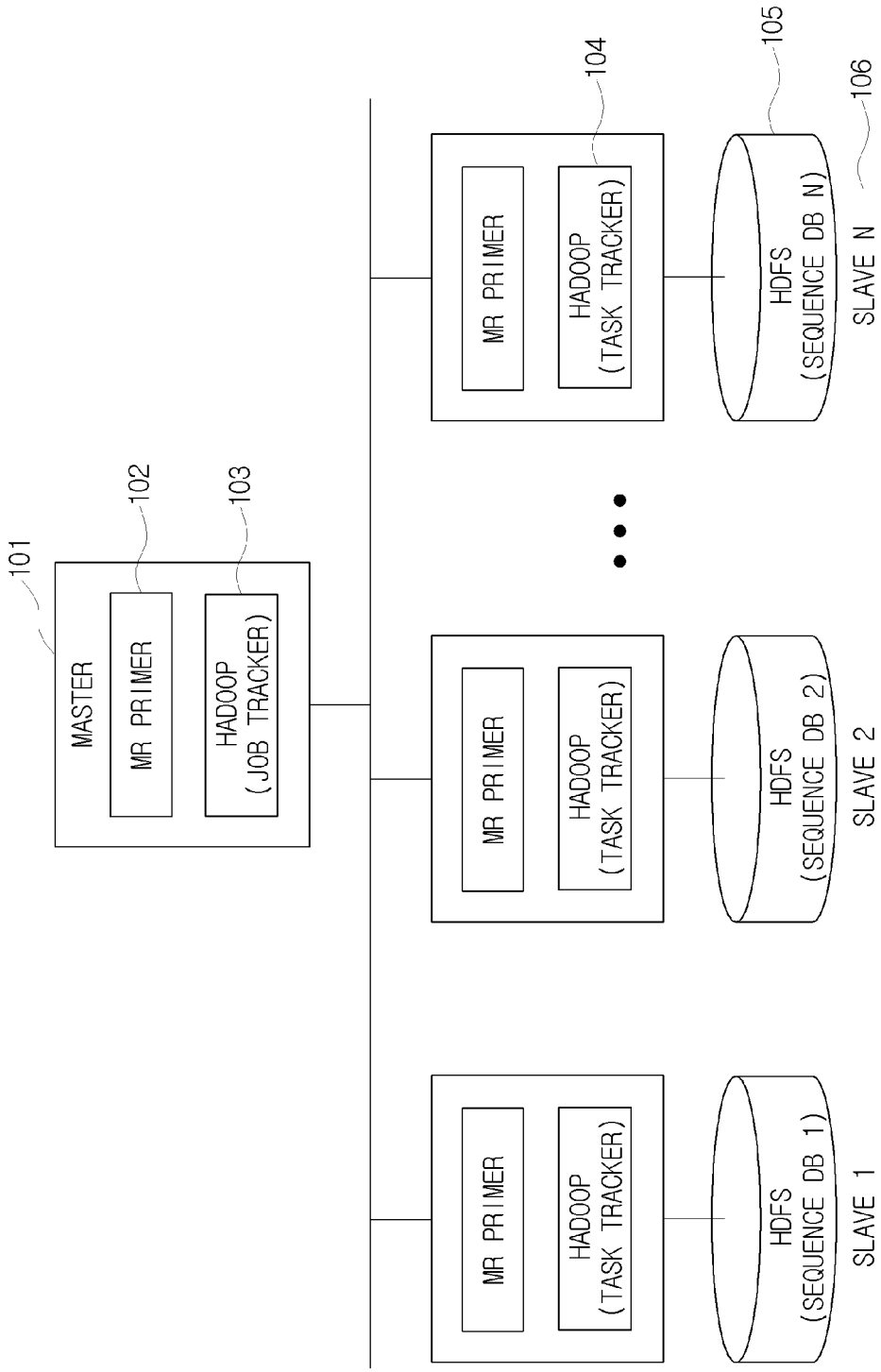
FIG. 2 is a diagram showing the configuration of a system intended to realize the present invention.

FIG. 2 is a block diagram of a system intended to realize the present invention. As shown in FIG. 2, the system mainly includes a MapReduce (MR) primer 102, a Hadoop 103 configured to drive the MR primer 102, and a Hadoop distributed file system (HDFS) 105. Here, a framework cluster of the Hadoop 103 and the HDFS 105 includes one master node 101 and a plurality of slave nodes 106.

The MR primer 102 is executed on the frameworks of the Hadoop 103 and the HDFS 105, and a DNA sequence database provided by a user is dividedly stored in the HDFS 105 of each of the slave nodes 106.

When a user executes a program for the MR primer 102 at the master node 101, the program is transferred to each of the slave nodes 106 to start execution of the program for DNA sequences stored in each HDFS 105.

A specific execution sequence of the program for the MR primer 102 is as shown in FIG. 3. That is, as shown in FIG. 3, low-level calculations upon executing the program for the MR primer 102 are performed by a job tracker 103 of the master node 101, and task trackers 104 of the slave nodes 106 in an aspect of the Hadoop framework.

FIG. 3 is a flowchart showing a method of designing all valid primers which satisfy the conditions for specificity to large-scale DNA sequences in a large-scale DNA sequence database according to one exemplary embodiment of the present invention.

As shown in FIG. 3, a given DNA sequence database is received, and candidate primers having partial sequences having all possible lengths between the minimum length and the maximum length are extracted (S301 and S302).

Thereafter, the primers which do not satisfy received single primer filtering conditions when the candidate primers extracted in S302 are subjected to the single primer filtering conditions are excluded (S303).

Then, Map1, which includes all the possible partial sequences obtained in S302, and Map2, which includes candidate primer sets satisfying the single filtering conditions obtained in S303, are pair-joined. Here, when the primers for Map1 and Map2 have the same sequences other than the 5' termini thereof, the primers for Map2 are removed (S304).

Subsequently, Map1, which includes all the possible partial sequences obtained in S302, and Map2, which includes candidate primer sets satisfying the single filtering conditions and 5' cross-hybridization filtering conditions obtained in S304, are pair-joined. Here, when the primers for Map1 have the same sequences as the primers for Map2 except the sequences having a given mismatch number (#mismatch), the primers for Map2 are removed (S305).

In this case, false-positive primers which still remain after S304 and do not satisfy general cross-hybridization filtering conditions are removed (S306).

The primers remaining from the results of S306 are divided into forward primer sets and reverse primer sets, and the primers which do not satisfy the filtering conditions for primer pairs in self-join calculation when the two divided forward and reverse primer sets are subjected to the filtering conditions are excluded (S310).

Then, penalty scores for the primer pairs passing S310 are calculated, and the primer pairs in the same sidset group are sequentially sorted according to the penalty scores so as to obtain the results of the sequentially sorted primer pairs (S311 and S312).

The above-described operation of S302 will be described in further detail with reference to FIG. 4.

Figure 4:
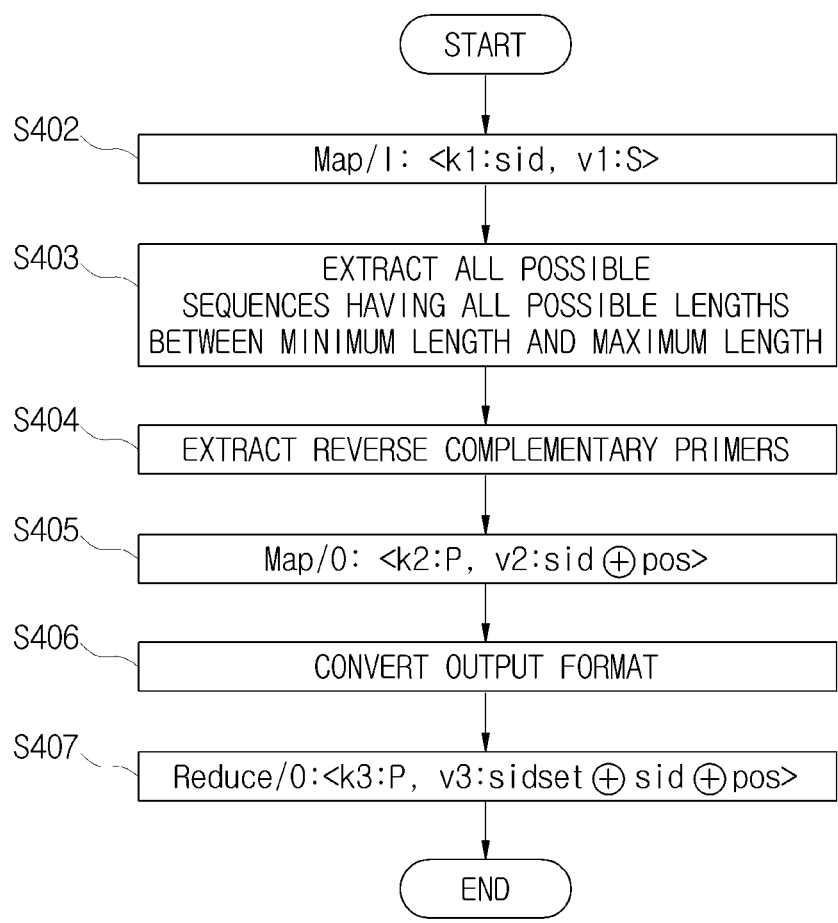
FIG. 4 is a detailed flowchart of a candidate primer extraction operation (S302) as shown in FIG. 3.

FIG. 4 is a detailed flowchart of a candidate primer extraction operation (S302) as shown in FIG. 3.

As shown in FIG. 4, in S402 and S403, Map receives the DNA sequence database in a format of a <k1:sid, v1:S> pair of a sequence identification number sid and sequence data S, and extracts the partial sequences for candidate primers having all possible lengths between the minimum length (minL) and the maximum length (maxL) in a window sliding manner.

That is, the partial sequences are sequentially extracted as the length increases from minL to maxL using |S|-minL as a starting point from 0 in a sequence having a length |S|. In this case, pos shown in FIG. 4 is a starting point, and P is a candidate primer for partial sequences having corresponding lengths between minL and maxL at the starting point pos. The minL and maxL length values are received from one of the single primer filtering conditions by a user. Next, in S404, Map also labels and extracts the reverse complementary primers. All the outputs of the Map are shuffled, and input into each of Reduces.

Then, in S406, an output format of each of the Reduces is converted into <k3:P, v3:sidset⊕sid⊕pos>, where P represents a primer candidate, sidset represents a set of sequence identification numbers of primers derived from P, sid represents the identification number of a certain sequence derived from P, and pos represents a position of P found in a sid sequence. Here, sidset, sid, and pos are combined by a ⊕ symbolic operator so that v3 becomes one text value.

In summary, a method of extracting the partial sequences, which have lengths between the minimum length minL and the maximum length maxL provided by a user, from the given DNA sequence database is performed by receiving the DNA sequence database in a format of a <k1:sid, v1:S> pair of a sequence identification number sid and sequence data S and extracting the partial sequences having lengths between the minimum length minL and the maximum length maxL.

Next, reverse complementary primers with respect to the extracted primers are tagged and extracted, and sidsets are generated as sets of sids represented by the same primers, thereby performing format conversions.

Also, the single filtering operation (S303) as shown in FIG. 3 will be described operation by operation with reference to FIG. 5.

Figure 5:
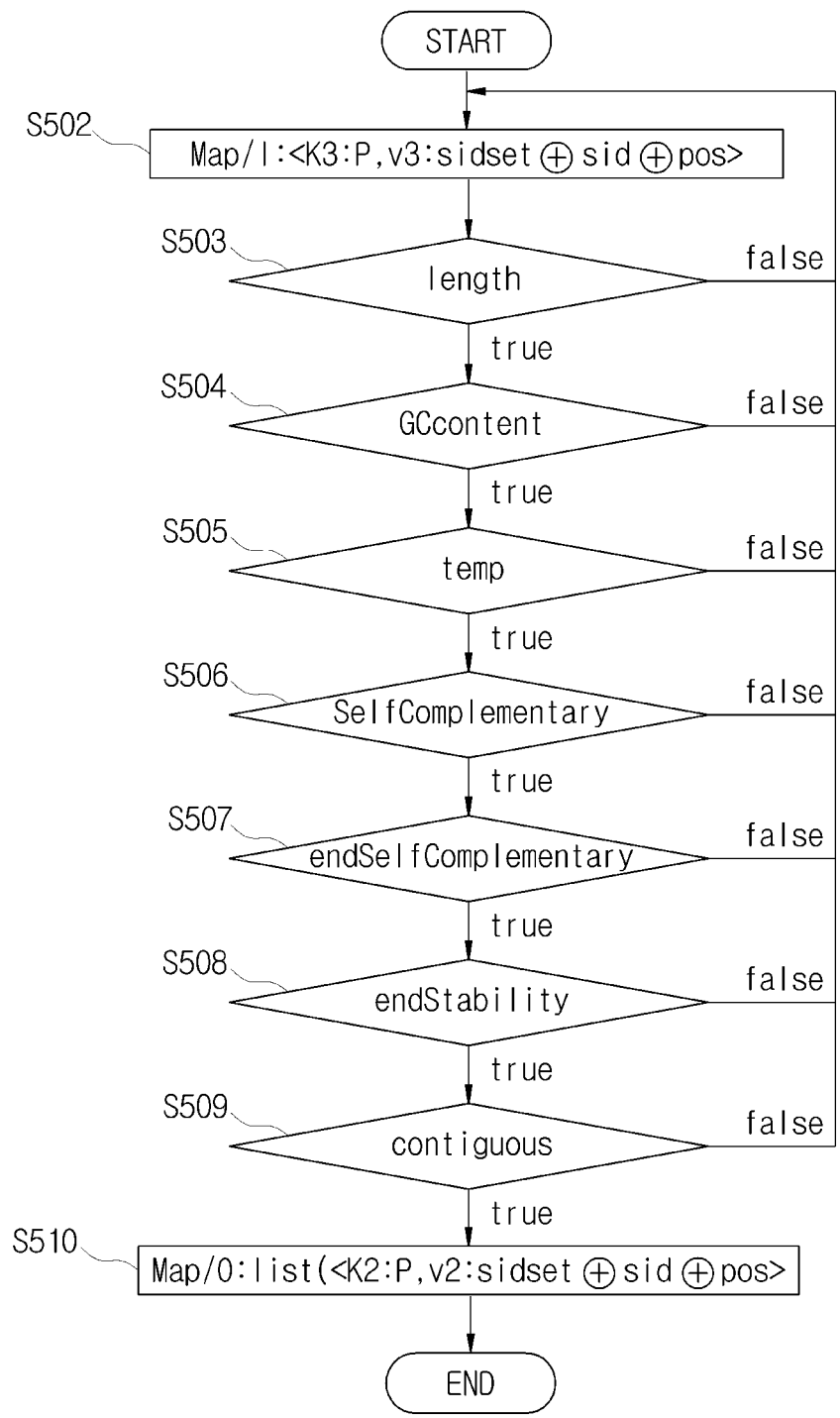
FIG. 5 is a detailed flowchart of a single filtering operation (S303) as shown in FIG. 3.

FIG. 5 is a detailed flowchart of the single filtering operation (S303) as shown in FIG. 3. In S303 shown in FIG. 3, seven single primer filtering conditions are applied to the candidate primers extracted in S302.

As shown in FIG. 5, the temperature (° C.), GC content (%), self-complementarity, 3'-end self-complementary, consecutive bases, and end stability (ΔG value) are sequentially determined as the filtering conditions, as described in S502 and S503 to S509. Here, the primer length is already determined in S302 shown in FIG. 3.

Values for all the conditions may be defined by a user. In particular, several formulas have been proposed to calculate the temperature. Among these, however, the most exact formula (for example, SantaLucia Jr, J. and Hicks, D. (2004) The thermodynamics of DNA structural motifs. Annu. Rev. Biophys. Biomol. Struct., 33, 415-440) known in the related art is applied in the present invention. Similarly, the most exact nearest neighbor thermodynamics method is also applied to calculate the end stability. Here, the Reduce functions are not used in S303 shown in FIG. 3.

In summary, a method of applying the single filtering conditions to the partial sequences extracted from the DNA sequence database as the candidate primers is performed by excluding the primers which do not satisfy seven single primer filtering conditions, such as temperature (° C.), GC content (%), self-complementarity, 3'-end self-complementarity, consecutive bases, and end stability (ΔG value), when the primers are subjected to the seven single primer filtering conditions.

Figure 6:
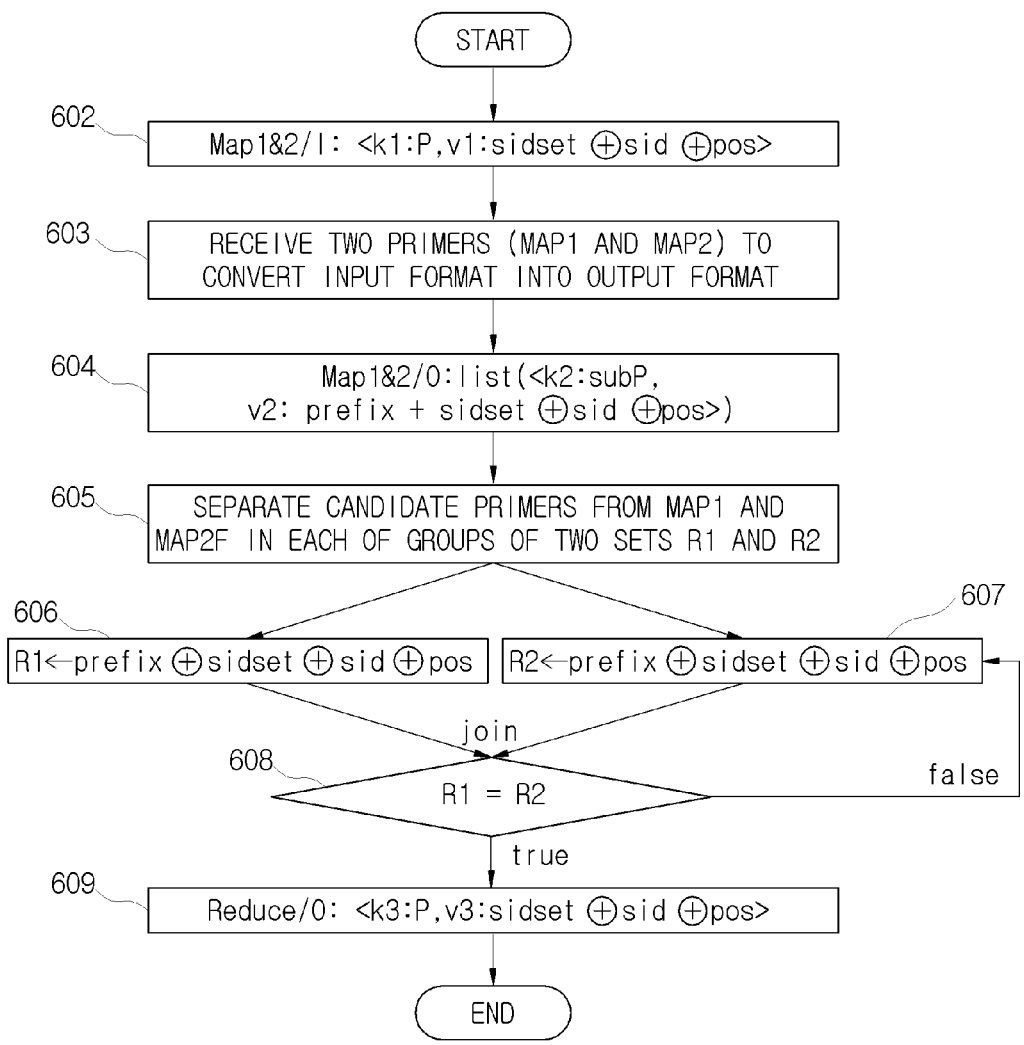
FIG. 6 is a detailed flowchart of a 5' cross-hybridization filtering operation (S304) as shown in FIG. 3.

Next, the operation of S304 shown in FIG. 3 will be described with reference to FIG. 6. FIG. 6 is a detailed operation flowchart of a 5' cross-hybridization filtering operation (S304) as shown in FIG. 3.

As shown in FIG. 6, both of Map1, which includes all the possible partial sequences extracted from the given DNA sequence database, and Map2, which includes candidate primer sets satisfying the single filtering conditions, are received (S603, S603, and S604). The goal of these operations is to remove the primer candidates which do not satisfy the 5' cross-hybridization filtering constraints.

Next, the candidate primers are separated from MAP1 and MAP2 in each of the groups of two sets R1 and R2 (S605).

Subsequently, the two sets R1 and R2 are pair-joined at the Reduce, and the primers for Map2 are removed when the primers for Map1 have the same sequences as the primers for Map2 except the 5' terminal region thereof while pair-joining the Map1 and the Map2 (S606 through S609).

In summary, a method of applying the 5' cross-hybridization filtering constraints to the candidate primers satisfying the single filtering constraints is performed by receiving both of the Map1, which includes all the possible partial sequences extracted from the given DNA sequence database, and the Map2, which includes candidate primer sets satisfying the single filtering conditions, and dividedly storing sequences having a certain length at the 5' termini thereof provided by a user and the other sequences.

Then, the primers for Map2 are removed when the primers for Map1 have the same sequences as the primers for Map2 except the 5' terminal region thereof while pair-joining the Map1 and the Map2.

One example of application of the 5' cross-hybridization filtering operation as described above will be described with reference to FIG. 7.

Figure 7:
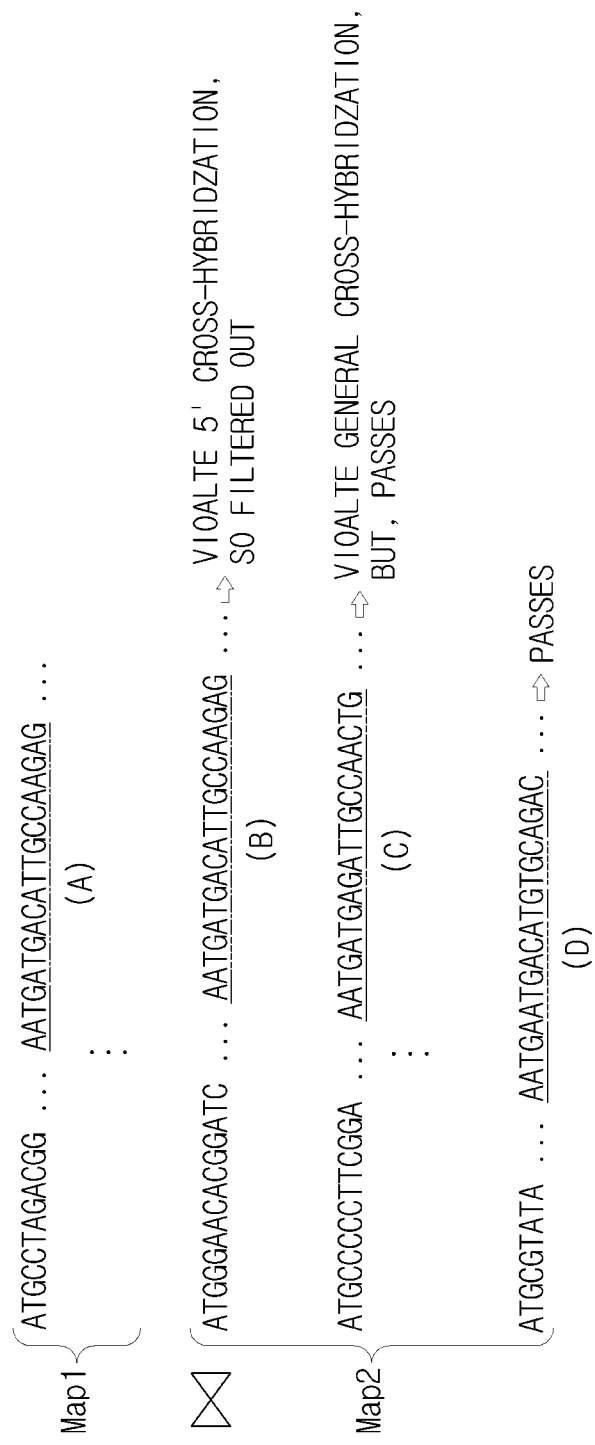
FIG. 7 is a schematic diagram showing an application of the 5' cross-hybridization filtering operation as shown FIG. 6; in Map 1: ATGCCTAGACGG is SEQ ID NO: 1, and AATGATGACATTGCCAAGAG is SEQ ID NO: 2; in Map 2: upper row-ATGGGAACACGGATC is SEQ ID NO: 3, and AATGATGACATTGCCAAGAG is SEQ ID NO: 2; middle row—ATGCCCCCTTCGGA is SEQ ID NO: 4 and AATGATGAGATTGCCAACTG is SEQ ID NO: 5; lower row—AATGAATGACATGTGCAGAC is SEQ ID NO: 6.

FIG. 7 is a schematic diagram showing an application of the 5' cross-hybridization filtering operation as shown FIG. 6; in Map 1: ATGCCTAGACGG is SEQ ID NO: 1, and AATGATGACATTGCCAAGAG is SEQ ID NO: 2; in Map 2: upper row-ATGGGAACACGGATC is SEQ ID NO: 3, and AATGATGACATTGCCAAGAG is SEQ ID NO: 2, middle row—ATGCCCCCTTCGGA is SEQ ID NO: 4 and AATGATGAGATTGCCAACTG is SEQ ID NO: 5; lower row—AATGAATGACATGTGCAGAC is SEQ ID NO: 6;

As shown in FIG. 7, the primer (b) for Map2 is removed when the primer (b) for Map2 has the same sequence as the primer (a) for Map1 except the 5' terminal region thereof. Then, a primer (c) for Map2 should be removed since the primer (c) for Map2 has a sequence very similar to the primer (a) for Map1, but will be removed in the next operation, that is, a general cross-hybridization filtering operation, since the primer (c) for Map2 do not violate the 5' cross-hybridization constraints.

Meanwhile, a specific operation (S306) shown in FIG. 3 will be described with reference to FIG. 8.

Figure 8:
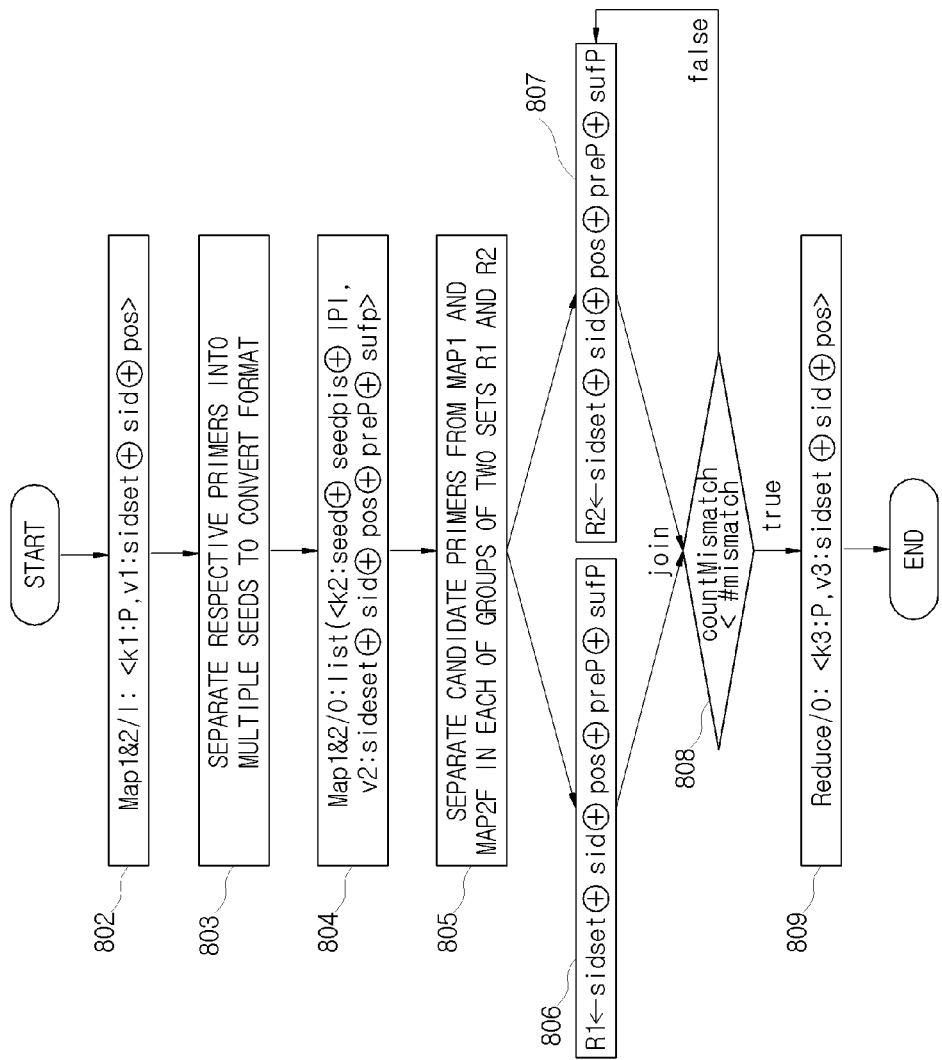
FIG. 8 is a detailed flowchart of a general cross-hybridization filtering operation (S306) as shown in FIG. 3.

FIG. 8 is a detailed flowchart of a general cross-hybridization filtering operation (S306) as shown in FIG. 3.

Referring to FIG. 8, both of Map1, which includes all the possible partial sequences extracted from the given DNA sequence database, and Map2, which includes candidate primer sets satisfying the single filtering conditions and the 5' cross-hybridization filtering conditions, are received.

Next, the primers for Map2 are removed when the primers for Map1 have the same sequences as the primers for Map2 except the sequences having a given mismatch number (#mismatch) while pair-joining the Map1 and the Map2.

To effectively perform this operation, in S803, Map divides each of the primers into a plurality of seeds, converts the seeds from a format of <k1:P, v1:sidset⊕sid⊕pos> into a format of (<k2:seed, v2:sidset⊕sid⊕pos⊕preP⊕sufP>), and stores the formats.

The lengths of seeds that may be generated from one primer may be defined as follows. The number (⌊m/(k+1)⌋) of exactly matched bases are included in a sequence including k mismatches and having a length of m. In an output format, preP represents a left region of a seed of the primer, and sufP represents a right region of the seed of the primer. Therefore, the assembly of preP, seed, and sufP has the same sequence as the original primer.

All the outputs of the Map are shuffled, and all the primers derived from Map1 and Map2 having the same seeds are input into a certain Reduce. Therefore, it is possible to determine whether the primer sets having the same seeds satisfy the general cross-hybridization filtering conditions at each of the Reduses.

In summary, a method of applying the general cross-hybridization filtering conditions to the candidate primers satisfying the single filtering conditions and the 5' cross-hybridization filtering conditions is performed by receiving both of the Map1, which includes all the possible partial sequences extracted from the given DNA sequence database, and the Map2, which includes candidate primer sets satisfying the single filtering conditions and the 5' cross-hybridization filtering conditions, dividing each of the Map1 and the Map2 into a plurality of seeds, and storing the plurality of seeds.

Then, the primers for Map2 are removed when the primers for Map1 have the same sequences as the primers Map2 except the sequences having a given mismatch number (#mismatch) while pair-joining the Map1 and the Map2. This operation will be described with reference to FIGS. 9A and 9B.

FIGS. 9A and 9B are schematic diagrams showing an application of the operations (S306 and S308) as shown in FIG. 3.

As shown in FIG. 9A, when compared to the primer (a) for Map1, primers (c) and (d) for Map2 have two and ten mismatch bases, respectively. When one mismatch base is checked (#mismatch=1), the length of a seed is 9 as shown in FIG. 9B, and thus the primers (a), (c), and (d) have no common seeds. Therefore, the primers (c) and (d) are not collected in the Reduce together with the primer (a), or not removed.

However, the length of the seed at the next iteration (#mismatch=2) is 6, and thus common seeds are present between the primers (a) and (c), and between the primers (a) and (d). The primers (a) and (c) are collected in a certain Reduce, and the number of the mismatch bases in preP and sufP is proven to be 2. As a result, the primer (c) is removed.

Also, since there are so many mismatch bases between the primers (a) and (d), the primer (d) is not removed. When the primers successfully pass, v3:filtered is output to be true at the Reduce, and otherwise output to be false.

FIG. 10 is a detailed flowchart of an operation S308 as shown in FIG. 3. At the above-described operation, false-positive primers which do not satisfy the general cross-hybridization filtering conditions may still exist.

For example, the primer (d) passes when the primer (d) is tested as shown in FIG. 9. However, the primer (d) should be removed since the primer (d) has a sequence very similar to other primers (b) in Map1. In the iteration of #mismatch=2, three seeds may be generated from the primer (d). As a result, a total of three output pairs are generated in a <k3, v3> format as the outputs for the primer (d) at the Reduce in S1004. Among these, the filtering results of the primer (d) tested against the primer (a) are proven to be true, but the filtering results of the primer (d) tested against the primer (b) are proven to be false. In both cases, since the primer sets have the same format of sidset⊕P⊕sid⊕pos as k2, the primer sets are collected in the same Reduce. When one filtering result is proven to be false in S803 shown in FIG. 8, the Reduce does not output the corresponding primer in S804 shown in FIG. 8. Therefore, the primer (d) is removed in this example.

FIG. 11 is a detailed flowchart of a pair filtering operation (S310) as shown in FIG. 3.

As shown in FIG. 11, at S1103, the results of the previous operation are converted into a format of <k2:sid, list(v2: sidset⊕P⊕pos)> at the Map, and all the primer candidates having the same sid are collected in a certain Reduce.

Thereafter, the Reduce divides the candidate primers into two sets, such as a forward primer set and a reverse primer set, and self-join calculations are performed on the two sets (S1105 through S1117).

In the self-join calculations, five filtering conditions for primer pairs are applied at the Reduce. As described in S1108 through S1112, the difference in temperature, the difference in length, a product length, pair-complementarity, and 3'-end pair-complementarity are sequentially tested as the filtering conditions. All these values may be defined by a user when the program is executed.

Then, f.P, r.P, f.pos, and r.pos are output at the Reduce to represent a forward primer, a reverse primer having a pair with the position of f.P, and a position of r.P, respectively, (S1113). In summary, a method of applying the pair filtering conditions to the candidate primers satisfying the single filtering conditions, the 5' cross-hybridization filtering conditions, and the general cross-hybridization filtering conditions is performed by grouping the candidate primers having the same sids through format conversion.

Subsequently, the candidate primers belonging to the group are divided into two sets of unlabeled forward primers and labeled reverse primers according to a label introduced when the candidate primers are extracted from the DNA sequence database.

Then, the primers which do not satisfy five pair primer filtering conditions (the difference in length, the difference in temperature, a product length, pair-complementarity, and 3'-end pair-complementarity) are removed when the primers are subjected to the pair primer filtering conditions.

FIG. 12 is a detailed flowchart of the last operation, that is, a primer sorting operation (S311) as shown in FIG. 3.

Since all the primer pairs designed to pass S310 as shown in FIG. 3 are not effective for screening for a target sequence due to the difference in constraints, all the primer pairs are sorted in S311 according to the calculated penalty scores.

That is, as shown in FIG. 12, in S1203, the Map calculates a penalty for each of the forward and reverse primers (single primer penalty), and then calculates a pair primer penalty as the sum of the two penalties.

The primer penalties for the forward and reverse primers are obtained by calculating penalties of the primers with respect to the above-described single filtering constraints, which include length, temperature, GC content, self-complementarity, 3'-end self-complementarity, and end stability. That is, the two single penalties of the forward and reverse primers are added, and the penalties calculated with respect to the above-described pair filtering constraints are added to the sum of the single penalties.

The pair filtering constraints include the difference in length, the difference in temperature, a product length, pair-complementarity, and 3'-end pair-complementarity. After the penalties of the primer pairs are calculated, the Map outputs the filtering results in a format of <k2:<sidset, penalty>, v2:sid⊕f.P⊕f.pos⊕r.P⊕r.pos> in S1204. Here, k2 is output as a pair of sidset and penalty.

To sort the primer pairs according to the calculated penalties, the primer pairs undergo a partitioner operation (S1205) and a comparator operation (S1206).

In the partitioner operation (S1205), the primers are grouped according to the same sidset, and sent to a certain Reduce.

Next, the order of the primers is given based on the penalties in keys in the partitioned group.

Subsequently, in the last operation (S1207), an output format is converted into <k3:sidset⊕f.P⊕r,P, v3:sid⊕f.pos⊕r.pos>, where a primer pair <f.P, r.P> is found at a position of <f.pos, r.pos> in a sequence having the corresponding sid.

In summary, a method of calculating the penalties of the primer pairs to sort the primer pairs in the corresponding sidset groups is performed by calculating penalties of the respective forward and reverse primers corresponding to the pair primer filtering conditions.

Then, a pair primer penalty corresponding to the pair filtering condition is calculated, and added to the sum of the two calculated penalties.

Subsequently, the primers are grouped according to the sidsets, and sent to a certain Reduce, the order for the grouped primers is given based on the calculated penalties, and an output format is converted.

According to exemplary embodiments of the present invention, the method can be useful in designing all coverage of valid primer pairs which satisfies the various filtering constraints provided by users with respect to the given sequence database and has validated specificity to given sequences in the given sequence database.

Also, the method according to exemplary embodiments of the present invention has no errors during an operation of determining the validity since the design of primers is determined using a single/pair filtering constraint and homology tests as one integrated method even when a user does not use an additional tool.

In addition, 37,236,621 primers and 48,532,297 primers which can be used to amplify 97% and 95% of the sequences in the sequence database, respectively, in the experiments on the entire consensus coding sequences (CCDS) data from 29,064 humans genes and 23,874 mouse genes were able to be designed based on the experimental results according to exemplary embodiments of the present invention.

Also, the primers had a coverage of up to 25 in the case of the humans, and a coverage of up to 20 in the case of the mice. Therefore, since the primers designed in the present invention have a coverage of 1 or more, a user can use designed primers instead of the degenerate primers instead of the established primers without performing an additional validity test.

In the aspects of efficiency and extendability of computer clusters, the method of the present invention is very effective in designing all possible primer pairs from the entire human or mouse CCDS sequence database within one or two hours using 40 computer clusters, or within two or three hours using 10 computer clusters. Also, all the possible primer pairs can be designed from the DNA sequence data from 105,180 humans within seven hours using 40 computer clusters.

The method according to exemplary embodiments of the present invention can be used to design full sets of primer pairs, and thus be repeatedly used in PCR experiments when the primer results obtained once for a given input sequence database are established into a database as long as the filtering conditions are not changed. Generally, since the filtering conditions used in laboratories are hardly changed, a huge and complete primer database can be established by executing a program once on biological species whose sequence data exists in a sequence database and storing the resulting sequence data in the database.

Further, because the method according to exemplary embodiments of the present invention is based on the MapReduce framework having the scale-out characteristics, the method can be useful in further reducing a time required to obtain the primers by adding more computer into clusters.

Although the method for designing all valid primers, which satisfies the conditions for specificity to large-scale DNA sequences in a large-scale DNA sequence database, according to exemplary embodiments of the present invention has been described with reference to embodiments thereof, it will be apparent to those skilled in the art that various modifications can be made to the above-described exemplary embodiments of the present invention without departing from the scope of the invention. Thus, it is intended that the present invention cover all such modifications provided they come within the scope of the appended claims and their equivalents.

What is claimed is:

1. A method of performing a polymerase chain reaction (PCR), the method comprising:

executing, by a master node apparatus, a program for processing a genomic-scale DNA sequence database for at least one species, wherein the genomic-scale DNA sequence database includes several tens to hundreds of thousands of DNA sequences;

storing, by a plurality of slave node apparatuses, the genomic-scale DNA sequence database, receiving, by the plurality of slave node apparatuses, the program from the master node apparatus responding to the executing the program in the master node apparatus, executing, by the plurality of slave node apparatuses, the received program for processing the stored genomic-scale DNA sequence database, wherein processing the DNA sequence database comprises:

receiving a first candidate primer group consisting of a plurality of sequences for forward primers and reverse primers from the genomic-scale DNA sequence database, wherein each sequence of the sequences has a length between a minimum length and a maximum length;

selecting a second candidate primer group for forward primers and reverse primers by excluding at least one first sequence from the first candidate primer group, wherein the at least one first sequence does not satisfy single filtering conditions for each of forward primer and reverse primer; do not satisfy input single filtering conditions;

removing at least one second sequence from the second candidate primer group, wherein the at least one second sequence has the same sequences as at least one sequence in the first candidate primer group other than 5'termini thereof;

removing at least one third sequence from the second candidate primer group wherein the at least one third sequence has the same sequences except for a given number of mismatch with at least one sequence in the first candidate primer group;

removing at least one fourth sequence from the second candidate primer group wherein the at least one fourth sequence does not satisfy general cross-hybridization filtering conditions;

dividing the second candidate primer group after the removing processes into forward primer sets and reverse primer sets;

pairing each primer pair of all primer pairs with the forward primer set and reverse primer set, and removing at least one pair from the all primer pairs, wherein the at least one pair does not satisfy pair primer set filtering conditions;

calculating penalty scores for each of target primer pairs which satisfies the pair primer set filtering conditions in the all primer pairs and sorting the target primer pairs according to the calculated penalty scores; and converting the sorted target primer pairs into output format; and applying at least one primer pair of the sorted target primer pairs in the polymerase chain reaction.

2. The method of claim 1, wherein the single filtering conditions include temperature (OC), GC content (%), self-complementarity, 3'-end self-complementary consecutive bases, and end stability (a $\Delta G$ value).

3. The method of claim 1, wherein dividing the second candidate primer group comprises:

grouping candidate primers having the same identification number through format conversion in the second candidate primer group; and dividing the candidate primers into two sets of unlabeled forward primers and labeled reverse primer set according to a label introduced when the candidate primers are extracted from the genomic-scale DNA sequence database.

4. The method of claim 1, wherein calculating penalty scores for each of the target primer pairs comprises:

calculating penalty scores of each of the forward and the reverse primer of the target primer pairs which correspond to single primer filtering conditions;

calculating a pair primer penalty score corresponding to the pair primer set filtering conditions; and summing the pair primer penalty score and each of the penalty scores for the forward primer and the reverse primer.

5. The method of claim 1, wherein the target primer pairs are for multiple target nucleic acid sequences.

6. The method of claim 1, wherein the pair primer set filtering conditions include product length and at least one selected from the group consisting of difference in temperature, difference in length, pair-complementarity and 3'-end pair complementarity.

* * * * *